(12) United States Patent
Ghorbanian et al.

(10) Patent No.: US 10,039,444 B1
(45) Date of Patent: Aug. 7, 2018

(54) FREE SIZE LARYNGOSCOPE BLADE

(71) Applicants: Ehsanollah Ghorbanian, Mashhad (IR); Mohammad Gharavifard, Mashhad (IR)

(72) Inventors: Ehsanollah Ghorbanian, Mashhad (IR); Mohammad Gharavifard, Mashhad (IR)

( * ) Notice: Subject to any disclaimer, the term of this patent is extended or adjusted under 35 U.S.C. 154(b) by 0 days.

(21) Appl. No.: 15/425,179

(22) Filed: Feb. 6, 2017

(51) Int. Cl.
*A61B 1/267* (2006.01)
*A61B 1/07* (2006.01)

(52) U.S. Cl.
CPC .............. *A61B 1/267* (2013.01); *A61B 1/07* (2013.01)

(58) Field of Classification Search
CPC .................................. A61B 1/267; A61B 1/07
USPC ................. 600/190, 193, 196, 199
See application file for complete search history.

(56) References Cited

U.S. PATENT DOCUMENTS

| | | | | |
|---|---|---|---|---|
| 4,360,008 A | * | 11/1982 | Corazzelli, Jr. | A61B 1/267 600/120 |
| 5,036,835 A | * | 8/1991 | Filli | A61B 1/267 600/196 |
| 5,381,787 A | * | 1/1995 | Bullard | A61B 1/0056 600/188 |
| 6,135,948 A | * | 10/2000 | Lee | A61B 1/267 600/131 |
| 2014/0066721 A1 | * | 3/2014 | Dillard | A61B 18/1477 600/240 |
| 2016/0120394 A1 | * | 5/2016 | McGrath | A61B 1/00142 600/188 |

* cited by examiner

*Primary Examiner* — Pedro Philogene
*Assistant Examiner* — David C Comstock
(74) *Attorney, Agent, or Firm* — Azadeh Saidi

(57) ABSTRACT

A new Laryngoscopy blade having variable size blade is designed. This blade can supply the necessary length and appropriate view for Laryngoscopy without repeated blade changing.

16 Claims, 5 Drawing Sheets

104

FREE SIZE LARYNGOSCOPE BLADE

FIELD OF THE INVENTION

The present invention relates to laryngoscopes, and particularly to an improved blade for a laryngoscope.

BACKGROUND OF THE INVENTION

Laryngoscope is a tool for Tracheal intubation in patients who need anesthesia or have breathing difficulties. During CPR and anesthesia in surgery room, the use of a Laryngoscopy is inevitable. All the hospital wards, rescue teams and emergencies have to be equipped with Laryngoscope and know how to use it.

While a laryngoscope may be used to visually examine the larynx, its more important function is to aid in endotracheal intubation. The need for intubation may arise during a controlled situation, such as surgery, or in a crisis situation when the patient is unable to breathe adequately and requires a resuscitation bag or mechanical ventilation. During intubation, a flexible tube is inserted through the nasal or oral cavity, passed through the larynx, and into the trachea for the administration of gases. The larynx may be viewed as a chamber bounded superiorly by the epiglottis, inferiorly by the vocal cords which cover the opening to the trachea, anteriorly by the thyroid cartilage or Adam's apple, and posteriorly by a portion of the pharynx.

The laryngoscope generally comprises a handle, a blade which is used to move the patient's tongue out of the way and to lift the epiglottis to expose the vocal cords, and a light source to illuminate the glottis and vocal cords.

A Laryngoscope includes the following parts:
A. Handle and power supply battery.
B. Blade with embedded lighting source.

Two types of laryngoscopes are traditionally used by practitioners. The first type is generally called a MacIntosh blade. A MacIntosh blade is curved along its length and has a straight distal tip that is adapted to move the entire connecting tissue superior to the epiglottis of a patient to expose the aditus of the larynx. The second type of laryngoscope is generally called the Miller blade. The Miller blade is generally straight along its length and has a curved distal tip that is adapted to engage the epiglottis to expose the aditus of the larynx. The type of blade used depends on both the patient's anatomy and the preference of the practitioner. Accordingly, hospitals typically stock both types of blades in various sizes.

One of the problems of using the conventional blades is the selection of an appropriate blade for better observation of a Laryngoscope. Currently there are blades with specific sizes that a practitioner may use. As a result the perfect size is estimated based on a patient's age and sex, however this selection is simply an estimate and is not perfectly the needed size for the patient.

None of the blade evaluation methods can determine the exact size for all patients with the similar specifications. Anatomic differences and emergency condition put the inexperienced doctors in difficult situations. In order to overcome the shortcomings a new blade was designed.

For the reasons stated above and for other reasons stated below which will become apparent to those skilled in the art upon reading and understanding the present specification, there is a need in the art for a multipurpose blade that is more effective and versatile than traditional blades.

SUMMARY OF THE INVENTION

The above-mentioned problems of current systems are addressed by embodiments of the present invention and will be understood by reading and studying the following specification. The following summaries of embodiments are made by way of example and not by way of limitation. The summaries may include more or less elements provided in the claims and are merely provided to aid the reader in understanding some of the aspects of the invention.

In one embodiment, a laryngoscope blade is provided. The blade includes a base, a relatively straight main blade portion and a curved moving portion and a curved distal tip. The blade includes a base, a relatively straight main blade portion; and a curved moving portion having a straight proximal end, a curved middle portion and a curved distal tip. The relatively straight main blade portion has a length that extends from the base and comprises an opening and a cavity large enough to telescopically house (sliding in and out) the proximal end of the curved moving portion. The middle curved moving portion comprises a length that extends from the main blade portion and has a width larger than the proximal length. The distal tip has a length that extends from the curved middle portion and is curved.

In another embodiment, another laryngoscope blade is provided. The blade includes a base, a relatively straight main blade portion; and a straight moving portion having a straight proximal end, a straight middle portion and a curved distal tip. The relatively straight main blade portion has a length that extends from the base and comprises an opening and a cavity large enough to telescopically house (sliding in and out) the proximal end of the straight moving portion. The middle straight moving portion comprises a length that extends from the main blade portion and has a width larger than the proximal length. The distal tip has a length that extends from the straight middle portion and is curved.

In both embodiments the moving portion has the proximal end of the moving portion of the blade is nestled inside the main body portion of the blade and can be extended outside of the main body portion by a length adjustment means (FIGS. 8,9). Wherein the length adjustment means comprises a push button and/or slide button and/or screw knob or any other means capable of moving the proximal portion outside of the main body.

DETAILED DESCRIPTION OF THE SPECIFICATION

Figure 1:
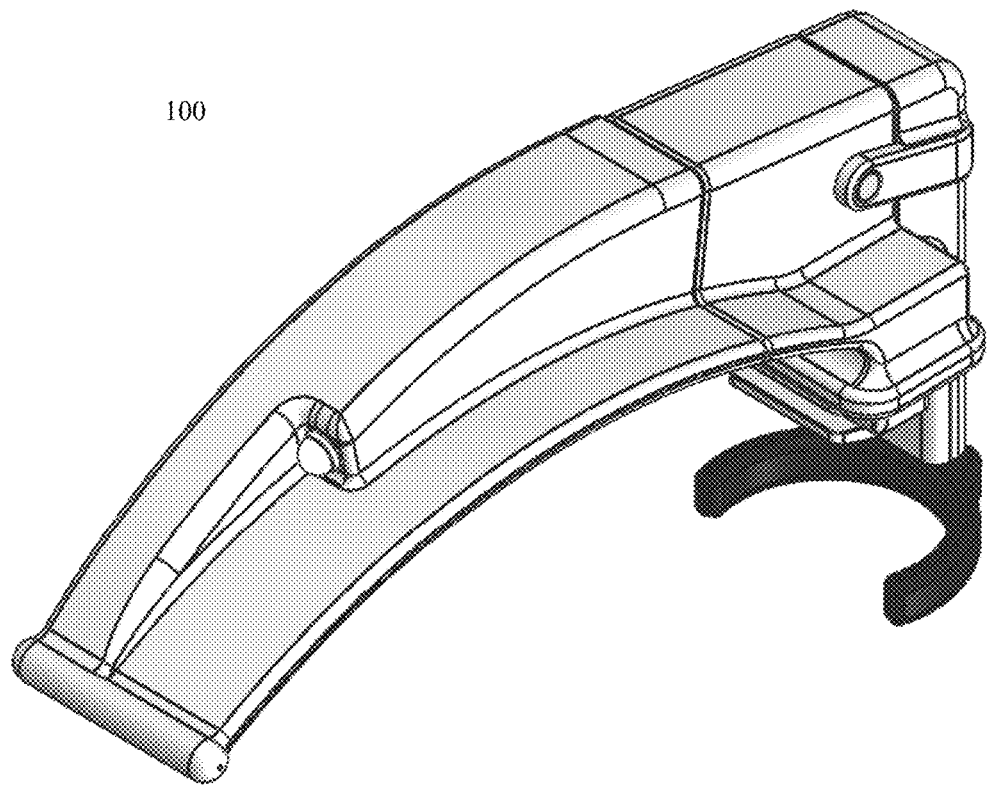
FIG. 1, displays a bent/curved laryngoscope blade having a variable length, at its minimum length.

Referring to FIG. 1, a top view of one embodiment of a blade 100 of the present invention is illustrated. The blade 100 includes a base 108 that is designed to be coupled to a laryngoscope handle via handle connector portion 131 (shown in FIGS. 2 and 6). Illustrated on the base 108 is a light port 107 designed to direct light from a light source 106 in the handle (not shown) to a light fiber 105 coupled to the blade 100. The blade 100 further includes a relatively straight main blade portion 110 that extends by a length from the base 108. A curved moving portion 103 is illustrated in FIG. 1, wherein a proximal end 104 of the curved moving portion 103 is nestled inside a space 109 of the main blade 110. Distal tip 102 further extends by a length from the moving blade portion 103.

Figure 4:
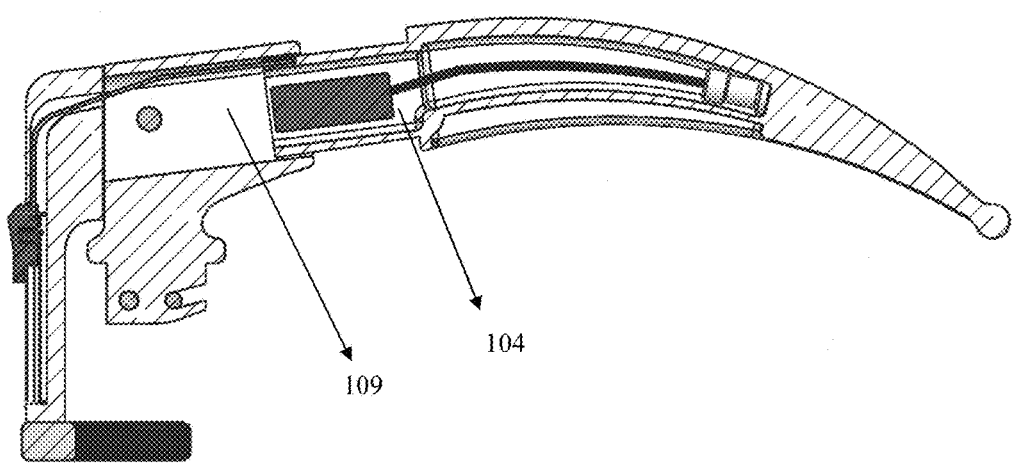
FIG. 4, displays a cross-sectional view of the same curved blade after a length adjustment.
Figure 7:
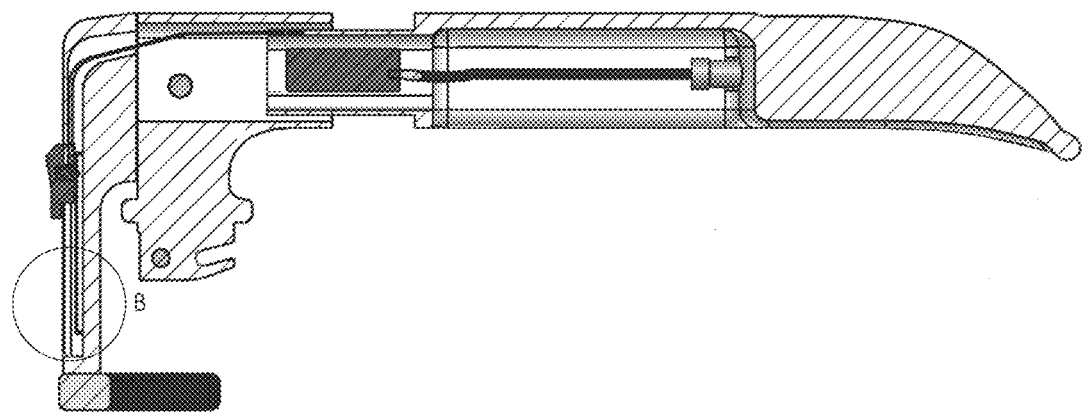
FIG. 7, displays a cross-sectional view of the same straight blade after the length adjustment.
Figure 8:
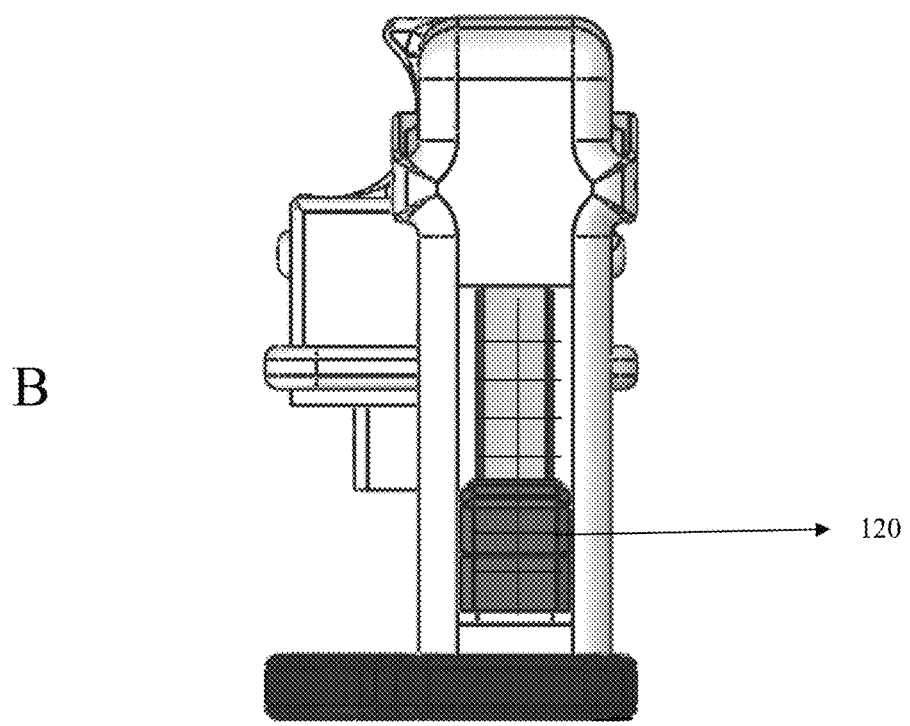
FIG. 8, displays an example of the blade's extension means before performing a length adjustment.
Figure 9:
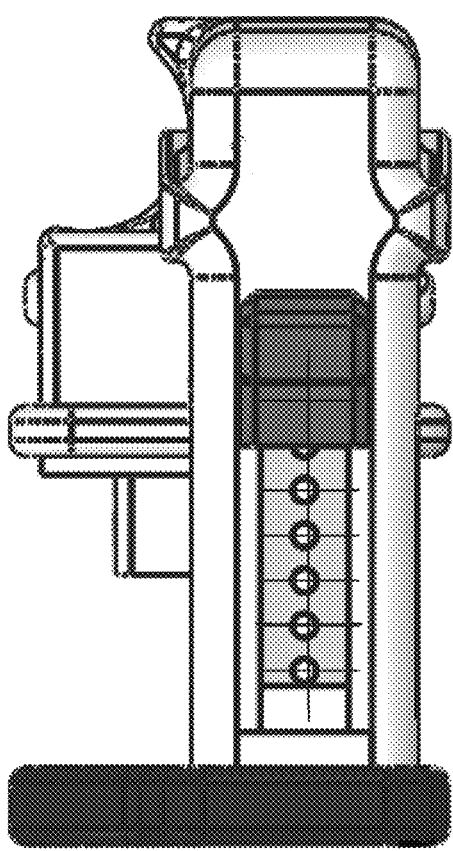
FIG. 9, displays an example of the blade's extension means after performing a length adjustment.

As illustrated in FIGS. 4 and 7, the proximal end 104 is narrower than the main blade portion 110 and the moving portion 103. That is, the proximal end 104 can easily move and/or slide back and forth inside the space 109 of the main blade portion 110, therefore allowing for the blade to have a variable length during the operation. The distal tip 102 in this embodiment has a shape that provides improved control of the epiglottis as well as an improved visual pathway to the aditus of the larynx by providing added control over tissue around the epiglottis.

The space 109 (FIGS. 4 and 7) accommodate the proximal end 104 of the moving part 103 and let it slide in longitudinal direction and/or rotational direction (telescopic manner) in and out of the main bade 110. The moving portion 103 is extended out and back inside in order to change the length of the entire blade via an adjusting length control means.

The adjusting length control means comprises a push button, and/or a rotating knob, and/or a spring and latch knob, and/or a latch and ladder shaped indentation, and/or pin and multiple hole, and/or any type of liquid keys, and/or piston type keys and/or other means of forcefully extending the proximal end 104 out of the main blade 110.

Figure 5:
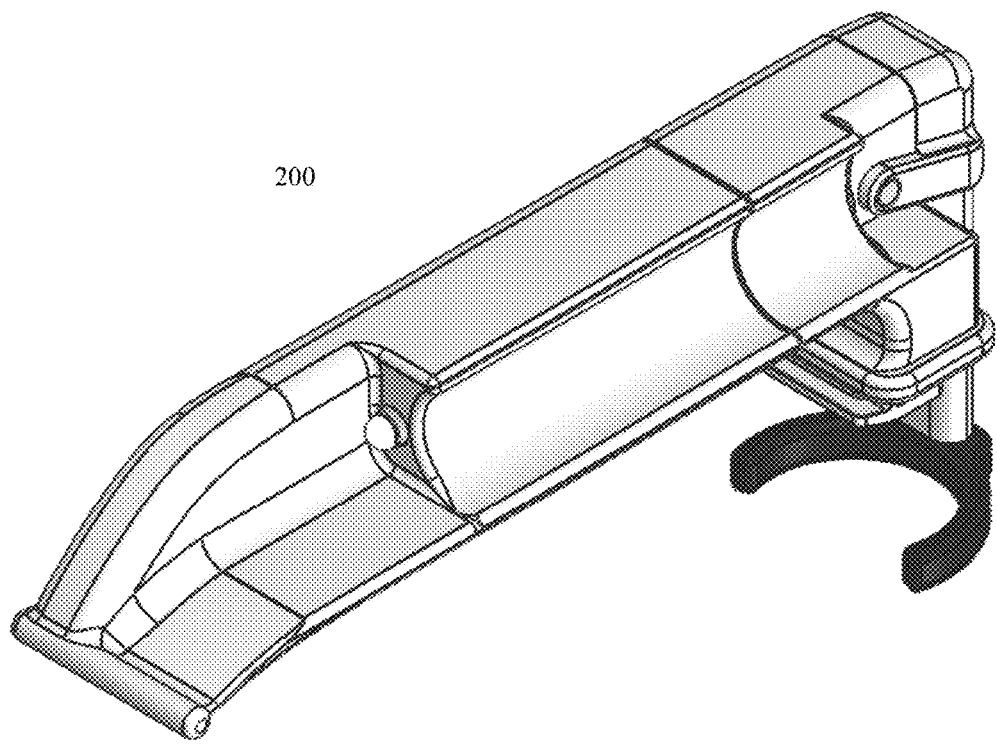
FIG. 5 is another embodiment of the invention, displaying a straight blade of a laryngoscope having a variable length (at its minimum length).

Referring to FIG. 5, a top view of another embodiment of a blade 200 of the present invention is illustrated. The blade 200 includes a base 108 that is designed to be coupled to a laryngoscope handle via handle connection portion 131. The blade 200 includes a base 108 that is designed to be coupled to a laryngoscope handle via handle connector portion 131 (shown in FIG. 6). Illustrated on the base 108 is a light port 107 designed to direct light from a light source 106 in the handle (not shown) to a light fiber 105 coupled to the blade 200. The blade 200 further includes a relatively straight main blade portion 110 that extends by a length from the base 108.

A straight moving portion 203 is illustrated in FIG. 7, wherein a proximal end 204 of the straight moving portion 203 is nestled inside a space 109 (FIG. 7) of the main blade 110. Distal tip 202 further extends by a length from the moving blade portion 203. As illustrated in FIG. 7, the proximal end 204 is narrower than the main blade portion 110 and the moving portion 203. That is, the proximal end 204 can easily move and/or slide back and forth inside the space 109 of the main blade portion 110, therefore allowing for the blade to have a variable length during the operation. The distal tip 202 in this embodiment has a shape that provides improved control of the epiglottis as well as an improved visual pathway to the aditus of the larynx by providing added control over tissue around the epiglottis.

Figure 2:
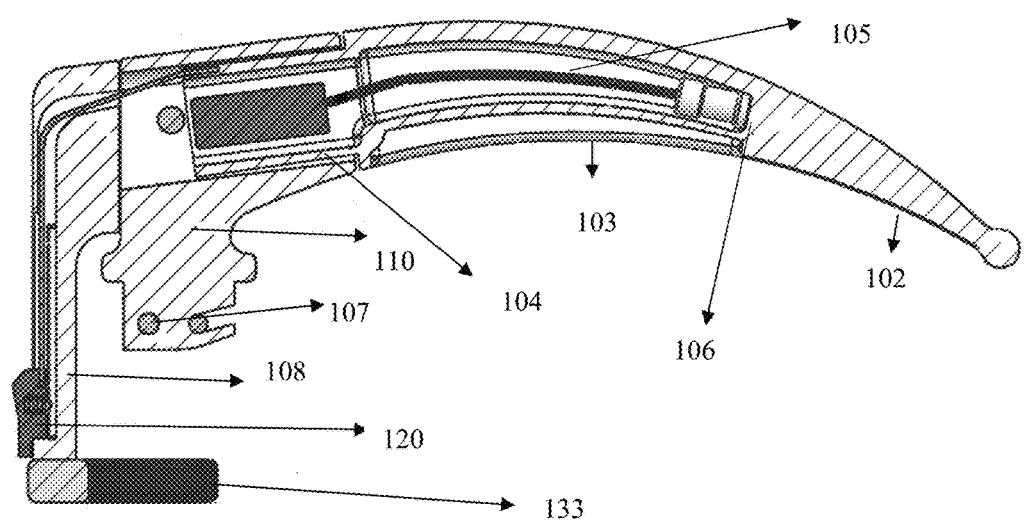
FIG. 2, displays a cross-sectional view of the same curved blade before length adjustment.
Figure 6:
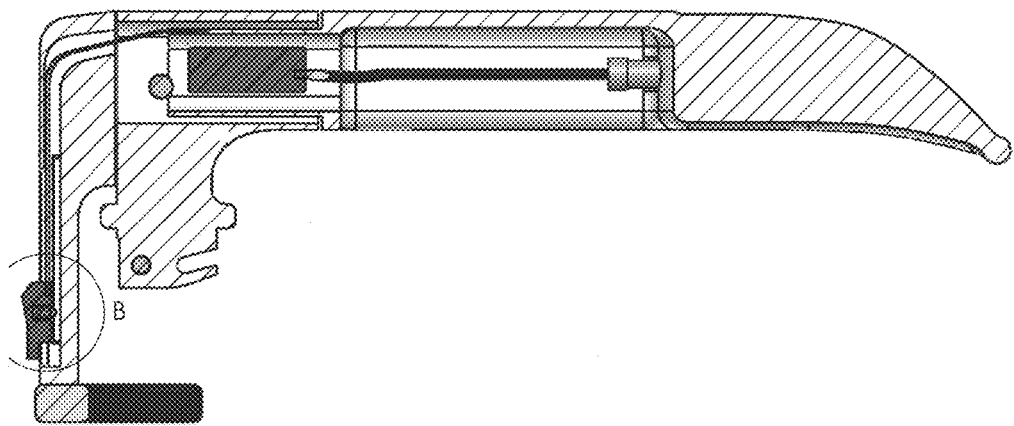
FIG. 6 displays a cross-sectional view of the same straight blade before the length adjustment.

When using the blade 100, the blade size is evaluated. The moving part 103/203 is pushed out, up to a necessary size and fixed with a stopping means (not shown). The lighting source (106, 206) has a wire (or fiber optic/not shown) 105/205 adjustable to the blade body length (FIGS. 2, 6). The blade of this invention as a whole has a function similar to all other standard straight or bent (disposable or reusable) blades with fixed length and is installed and fixed in the same way on the handle as them.

LIST OF ALL THE ELEMENTS 100, 200 Blade
102 Distal tip/end of the blade
103 Moving portion of the blade
104 Proximal end of the moving portion
105 Light fiber
106 Light source
107 Light port
108 Base
109 Internal space inside the main blade
110 Relatively straight main blade
120 Length adjusting means
131 handle connector portion The Laryngoscope blade 100/200; is made of a sheet of hard material (metal, composite or plastic) with the same width as the handle (Not shown). The Laryngoscope blade 100/200 of the present invention; when extended meets the standard size of all the blades currently used in this field and has more adjustable capabilities to accommodate for other blade length of any patient as needed. The blade meets the standard size considering diameter, length and general shape which are for example numbered 0-5. However the length adjusting means 120, comprises numbers (not shown) written around or along its side (depending on the type of the length adjusting means used) in order to provide enough information to the operator for adjusting the length of the blade to the suitable length.

Figure 3:
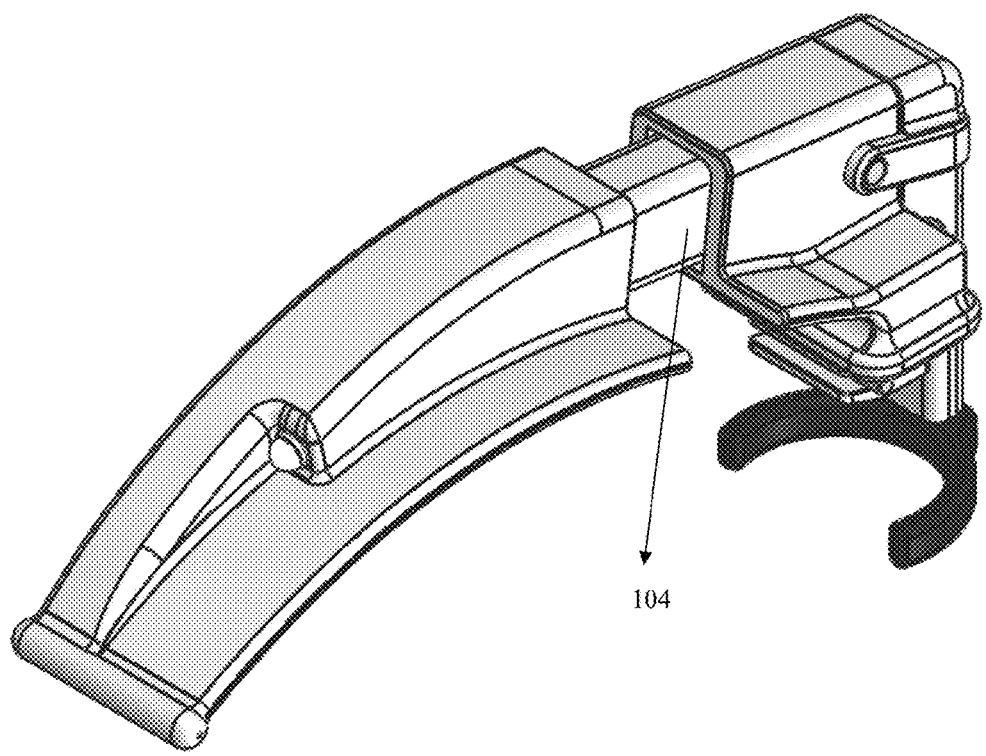
FIG. 3, displays the same blade at its maximum length while fully extended.

When the blade moving part 103; is extended longitudinally and/or rotates out (FIGS. 1, 3 and 7) all sizes of the Laryngoscope blade from minimum (FIGS. 1, 5) to maximum (FIGS. 3 and 7) is accounted for. Therefore the moving part 103; can adjust the entire length of the Blade 100/200; to all standard and abnormal sizes (for example size 3.5 or 1.2). Therefore as a result of this feature less harm is done to the patient and the physician can work with ease. Thus all the sizes are accessible without the need to change the current blade with a smaller or larger one.

Selecting appropriate blade size is difficult because of multiplication of blades and patients anatomic differences. But if only one blade could cover all sizes it would be effective and vital in emergency situations. While using this invented blade, the moving portion 103 of the blade 100/200 is pulled out to the needed length and fixed by a lock/stopping means (not shown). The stopping means comprises a pin and hole, latching gears, balls or a spring in a groove and other stooping means known in the art. Lighting source 106 has a connecting wire 105 with variable length adjusted to blade length.

The length of this blade 100/200 can be changed by the user before, during or after entering the throat. This ability provides the user an elbow room to use the blade in a classic way and with standard sizes. The blade diameter is between 0.2 to 10 centimeters and the length is variable from 3 to 50 cm. The blade's thickness can be between fractions of millimeters up to 5 centimeters. The angle between handle and blade 100/200 is fixed and optimized depending on the blade type and the material used. In curved blades, elongation will cause increase in curvature.

There are markers on a length of the blade, starting at a minimum value/length from where the proximal end 104 of the moving portion 103 is completely nestled inside space 109 and the rest of the numbers and markers are written and hacked on a length of the proximal end 104. Therefore as the operator pulls out the moving portion 103 from inside of main blade 110, he/she can set the length at the desired location. Also the same markers are written around or along the length adjusting means 120 in order to allow the operator to vary the length when the blade is inside the throat of the patient. The markers comprise units in inches, centimeters and/or other standard measurements known in the art.

The length of the blade can move back to its original length rapidly by releasing the stopping means, and/or the length could vary to a shorter length controllably by conjunctionally using the length adjusting means 120 and releasing the stopping means.

This blade functions the same as all the standard straight and curved blades known in the art and it is installed and fixed on a laryngoscope handle in the same way as what is known the in the art. Due to the adjustable length there will be a suitable view provided to the operator. As the classic form of the blade has been kept, the operator can achieve the necessary coordination rapidly.

The Blade comprises of material made of hard PVC compatible with medical utilization and/or metal and/or composite and/or polymers and soft or jell type covers based on the patient's needs. In case that washing and sterilizing is possible it can be reusable otherwise it's disposable.

In another embodiment in order to change the length of the blade an electrical or mechanical motor which is installed at the end of handle or blade; and which is connected to the moving blade can be used. Length and speed meter on the motor will display any changes to the length and the direction in which it is varying (increase or decrease).

In another embodiment the blade length can be varied by a bag filled with air or other liquids installed inside the handle, and/or at the end of the Laryngoscope blade when the user pushes the bag the liquid flows and drives the moving blade up and out longitudinally.

The invention claimed is:

1. A free size laryngoscope blade, comprising:
   a base configured and arranged to connect to a handle at one end;
   a relatively straight main blade portion having a length that extends from another end of said base, said main blade portion further having a cavity extending along a length of said main blade; and
   a singularly shaped consisting of one piece and not integrated moving blade portion having a distal tip and a proximal end, wherein said moving blade portion having an original length that extends from an end of said main body to said distal tip, wherein said proximal end having a length and a width, wherein said proximal width is smaller than a width of said moving blade portion, said distal tip having a bend at a select location about its length, and wherein said length and width of said proximal moving portion is the same as a length and width of said cavity of said main blade portion, allowing said proximal moving portion to telescopically nestle inside said cavity;
   a light port extending from said main body to said moving body portion accommodating an extendable light fiber connected to a light source.

2. The laryngoscope blade of claim 1, wherein said moving blade portion comprises a straight or curved midsection and/or combination of both.

3. The laryngoscope of claim 2, further comprising a stopping means and a length adjusting means on and/or inside said main blade portion.

4. The laryngoscope of claim 3, wherein said proximal moving portion moves/slides inside and out of said cavity varying a desired length of said moving blade portion between said original length and more than said original length covering a wide range of standard and un-normal length to meet a patient's needs.

5. The laryngoscope blade of claim 4, wherein said stopping means comprises various type of locks having parts and configurations that is used alone or in combination with each other as needed; locking said moving blade portion fixedly inside said cavity before and after said desired length is selected; wherein said various parts comprises any or a few of a lever; a spring latching ball; a pin and hole; latching gears, balls or a spring in a groove.

6. The laryngoscope of claim 5, wherein said cavity comprises a shape and volume the same as an entire volume of said proximal end.

7. The laryngoscope of claim 6, wherein said proximal moving end further having markers and number along its said length, and wherein said desired length can be selected based on said numbers and markers when said proximal moving end is extended in/out of said cavity.

8. The laryngoscope of claim 7, wherein said length adjusting means comprises various parts and configurations working alone or in combination with each other as needed and known in this art, comprising a push button, a rotating knob; a spring and latch knob; a latch and ladder shaped indentation; pin and multiple holes; any type of liquid keys; piston type keys; and electrical or mechanical means for forcefully extending said proximal moving end in/out of said main blade portion.

9. The laryngoscope of claim 8, wherein said lighting source is installed on said moving blade portion and/or on said main blade portion.

10. The laryngoscope of claim 9, wherein said length adjusting means comprises similar markers and numbers as the ones on said proximal moving portion, allowing said desired length to be adjusted and selected before, during and after said laryngoscope blade is entered inside said patient's throat.

11. The laryngoscope blade of claim 10, wherein said length adjusting means functions when said stopping means is released.

12. The laryngoscope blade of claim 11, wherein said moving blade portion and/or main blade portion made of a material compatible with medical utilization comprising hard PVC, and/or metal and/or composite and/or silicone material.

13. The laryngoscope blade of claim 12, wherein said moving blade can be removed entirely and replaced with a new one and/or washed to be used again, hence it being disposable and/or reusable.

14. The laryngoscope blade of claim 13, wherein said markers and/or numbers comprise standard size codes for blades and other sizes in between and beyond said standard size codes and wherein it further comprises length units (inches, centimeters) information as well, in order to determine said length of said moving blade portion as a whole.

15. The laryngoscope blade of claim 14, wherein said electrical and/or mechanical means are an electrical and/or mechanical motor that is installed at an end of said handle and/or main blade portion and is connected to said moving blade portion; wherein any changes to said desired length and speed of said motor is displayed on a small screen with an indication of a direction of increase or decrease of either one (plus and minus signs and/or utilization of green and red LED lights).

16. The laryngoscope blade of claim 15, wherein said length adjusting means further comprising a bag/bladder filled with air and/or other liquids installed inside said handle and/or at an end of said main blade portion, wherein when said bladder is pressed and squeezed down said liquid flows and drives said moving blade portion longitudinally and/or rotationally out from said cavity.

* * * * *